US008940238B2

(12) United States Patent
Tan et al.

(10) Patent No.: US 8,940,238 B2
(45) Date of Patent: *Jan. 27, 2015

(54) OPTICAL SENSOR OF BIO-MOLECULES USING THIN-FILM INTERFEROMETER

(71) Applicant: Access Medical Systems, Ltd., Palo Alto, CA (US)

(72) Inventors: Hong Tan, San Jose, CA (US); Yushan Tan, Shanghai (CN); Erhua Cao, Shanghai (CN); Ming Xia, Shanghai (CN); Robert F. Zuk, Menlo Park, CA (US)

(73) Assignee: Access Medical Systems, Ltd., Palo Alto, CA (US)

( * ) Notice: Subject to any disclaimer, the term of this patent is extended or adjusted under 35 U.S.C. 154(b) by 22 days.

This patent is subject to a terminal disclaimer.

(21) Appl. No.: 14/095,120

(22) Filed: Dec. 3, 2013

(65) Prior Publication Data

US 2014/0093432 A1    Apr. 3, 2014

Related U.S. Application Data

(63) Continuation of application No. 13/213,525, filed on Aug. 19, 2011, now Pat. No. 8,597,578, which is a
(Continued)

(51) Int. Cl.
*G01N 21/00* (2006.01)
*G01B 9/02* (2006.01)
(Continued)

(52) U.S. Cl.
CPC ............ *G01N 21/45* (2013.01); *G01N 21/7703* (2013.01); *G02B 6/262* (2013.01)

USPC .................. 422/82.11; 422/82.05; 422/82.09; 385/12; 385/15; 385/52; 385/53; 356/477; 356/478; 356/479; 356/480

(58) Field of Classification Search
None
See application file for complete search history.

(56) References Cited

U.S. PATENT DOCUMENTS 5,804,453 A    9/1998  Chen
6,028,666 A    2/2000  Boss et al.
(Continued)

FOREIGN PATENT DOCUMENTS

JP    2007-501403    1/2007

OTHER PUBLICATIONS

International Search Report and Written Opinion of International Application No. PCT/US2010/024801 with a mailing date of Sep. 29, 2010.

*Primary Examiner* — Neil N Turk
(74) *Attorney, Agent, or Firm* — Perkins Coie LLP; Viola T. Kung

(57) ABSTRACT

The present invention is directed to an assembly for use in detecting an analyte in a sample based on thin-film spectral interference. The assembly comprises a waveguide, a monolithic substrate optically coupled to the waveguide, and a thin-film layer directly bonded to the sensing side of the monolithic substrate. The refractive index of the monolithic substrate is higher than the refractive index of the transparent material of the thin-film layer. A spectral interference between the light reflected into the waveguide from a first reflecting surface and a second reflecting surface varies as analyte molecules in a sample bind to the analyte binding molecules coated on the thin-film layer.

15 Claims, 9 Drawing Sheets

Related U.S. Application Data continuation of application No. PCT/US2010/024801, filed on Feb. 19, 2010.

(60) Provisional application No. 61/208,215, filed on Feb. 20, 2009, provisional application No. 61/279,077, filed on Oct. 15, 2009.

(51) Int. Cl.
*G02B 6/26* (2006.01)
*G02B 6/36* (2006.01)
*G01N 21/45* (2006.01)
*G01N 21/77* (2006.01)
*G02B 6/00* (2006.01)
*G01N 21/63* (2006.01)

(56) References Cited

U.S. PATENT DOCUMENTS

| | | |
|---|---|---|
| 6,655,849 B1 | 12/2003 | Malavieille et al. |
| 7,319,525 B2 | 1/2008 | Tan et al. |
| 7,324,207 B1 | 1/2008 | Kirkpatrick et al. |
| 7,394,547 B2 | 7/2008 | Tan et al. |
| 2002/0159068 A1 | 10/2002 | Pfau et al. |
| 2008/0291456 A1 | 11/2008 | Ghislain |

OPTICAL SENSOR OF BIO-MOLECULES USING THIN-FILM INTERFEROMETER

This application is a continuation of U.S. application Ser. No. 13/213,525, filed Aug. 19, 2011; which is a continuation of PCT/US2010/024801, filed Feb. 19, 2010; which claims the priority of U.S. Provisional Application No. 61/208,215, filed Feb. 20, 2009; and 61/279,077, filed Oct. 15, 2009. The contents of the above-identified applications are incorporated herein by reference in their entirety.

TECHNICAL FIELD

This invention relates to an apparatus that improves detecting the presence, amount, or rate of binding of one or more analytes in a sample, and in particular an apparatus utilizing thin-film interferometer technology.

BACKGROUND OF THE INVENTION

Diagnostic tests based on a binding event between members of an analyte-anti-analyte binding pair are widely used in medical, veterinary, agricultural and research applications. Typically, such methods are employed to detect the presence or amount or an analyte in a sample, and/or the rate of binding of the analyte to the anti-analyte. Typical analyte-anti-analyte pairs include complementary strands of nucleic acids, antigen-antibody pairs, and receptor-receptor binding agent, where the analyte can be either member of the pair, and the anti-analyte molecule, the opposite member.

Diagnostics methods of this type often employ a solid surface having immobilized anti-analyte molecules to which sample analyte molecules will bind specifically and with high affinity at a defined detection zone. In this type of assay, known as a solid-phase assay, the solid surface is exposed to the sample under conditions that promote analyte binding to immobilized anti-analyte molecules. The binding event can be detected directly, e.g., by a change in the mass, reflectivity, thickness, color or other characteristic indicative of a binding event. Where the analyte is pre-labeled, e.g., with a chromophore, or fluorescent or radiolabel, the binding event is detectable by the presence and/or amount of detectable label at the detection zone. Alternatively, the analyte can be labeled after it is bound at the detection zone, e.g., with a secondary, fluorescent-labeled anti-analyte antibody.

U.S. Pat. No. 5,804,453 discloses a method of determining the concentration of a substance in a sample solution, using a fiber optic having a reagent (capturing molecule) coated directly at its distal end to which the substance binds. The distal end is then immersed into the sample containing the analyte. Binding of the analyte to the reagent layer generates an interference pattern and is detected by a spectrometer.

U.S. Pat. No. 7,394,547 discloses a biosensor that a first optically transparent element is mechanical attached to an optic fiber tip with an air gap between them, and a second optical element as the interference layer with a thickness greater than 50 nm is then attached to the distal end of the first element. The biolayer is formed on the peripheral surface of the second optical element. An additional reflective surface layer with a thickness between 5-50 nm and a refractive index greater than 1.8 is coated between the interference layer and the first element. The principle of detecting an analyte in a sample based on the changes of spectral interference is described in this reference, which is incorporated herein by reference.

U.S. Pat. No. 7,319,525 discloses a different configuration that a section of an optic fiber is mechanically attached to a tip connector consisting of one or more optic fibers with an air gap between the proximal end of the optic fiber section and the tip connector. The interference layer and then the biolayer are built on the distal surface of the optical fiber section.

An air gap between coupling fibers has several disadvantages. One drawback is the reduction in coupling efficiency. Another problem is poor alignment. Practically, it is difficult to maintain the same exact air gap size for different pairs of sensors and instruments. In addition, air-fiber interface tends to causing higher reflection back to the spectrometer that can decrease the measurement signal-to-noise ratio.

Although prior art provides functionality in utilizing biosensors based upon thin-film interferometer, there exists a need for improvements in the performance of the interferometer.

SUMMARY OF THE INVENTION

The present invention is directed to an assembly for use in detecting an analyte in a sample based on thin-film spectral interference. The assembly comprises a waveguide connector containing a waveguide, wherein the waveguide transports a light signal from a light source to the assembly, and the waveguide transports reflected light signals from the assembly to a detector. The assembly further comprises a monolithic substrate having a coupling side and a sensing side, the coupling side is coupled to the waveguide connector by a coupling hub, wherein the waveguide connector is engaged with the coupling hub to form a optical coupling between the waveguide and the monolithic substrate. The assembly further comprises a coupling medium located between the waveguide connector and the monolithic substrate so the end of the waveguide couples to the monolithic substrate without any gap. The assembly additionally comprises a thin-film layer directly bonded to the sensing side of the monolithic substrate, wherein the thin film layer comprises a transparent material, a first reflecting surface comprising a layer of analyte binding molecules, and a second reflecting surface between the thin film layer and the monolithic substrate. A spectral interference between light reflected into the waveguide from the assembly varies as analyte molecules in the sample bind to the analyte binding molecules.

In one embodiment, the coupling hub is inserted into the waveguide connector. In another embodiment, the waveguide connector is a ferrule and the ferrule is inserted into the coupling hub.

The present invention is also directed to an assembly comprising: (a) a waveguide; (b) a monolithic substrate having a coupling side and a sensing side, the coupling side is optically coupled to the waveguide; and (d) a thin-film layer directly bonded to the sensing side of the monolithic substrate. The waveguide transports a light signal from a light source to the assembly, and the waveguide transports reflected light signals from the assembly to a detector. The thin film layer comprises a transparent material, a first reflecting surface comprising a layer of analyte binding molecules, and a second reflecting surface between the thin film layer and the monolithic substrate. The refractive index of the monolithic substrate is higher than the refractive index of the transparent material of the thin-film layer; and the refractive index of the coupling medium is greater than 1.3, preferreably in between refractive indexes of the waveguide and the monolithic substrate. A spectral interference between light reflected into the waveguide from said first and said second reflecting surfaces varies as analyte molecules in the sample bind to the analyte binding molecules. In one embodiment, the assembly further comprises a conpling medium between the waveguide and the monolithic substrate, wherein the refractive index of the coupling medium is greater than 1.3.

DETAILED DESCRIPTION OF THE INVENTION

Definitions

Terms used in the claims and specification are to be construed in accordance with their usual meaning as understood by one skilled in the art except and as defined as set forth below.

"About," as used herein, refers to within ±15% of the recited value.

An "analyte-binding" molecule, as used herein, refers to any molecule capable of participating in a specific binding reaction with an analyte molecule. Examples include but are not limited to, (i) antigen molecules, for use in detecting the presence of antibodies specific against that antigen; (ii) antibody molecules, for use in detecting the presence of antigens; (iii) protein molecules, for use in detecting the presence of a binding partner for that protein; (iv) ligands, for use in detecting the presence of a binding partner; or (v) single stranded nucleic acid molecules, for detecting the presence of nucleic acid binding molecules.

A "ferrule" as used herein, refers to a rigid tube that confines or holds a waveguide as part of a connector assembly.

"A monolithic substrate," as used herein, refers to a single piece of a solid material such as glass, quartz, or plastic that has one refractive index.

A "probe," as used herein, refers to a monolithic substrate coated with a thin-film layer at the sensing side.

A "waveguide" as used herein, refers to a device (as a duct, coaxial cable, or optic fiber) designed to confine and direct the propagation of electromagnetic waves (as light); for example, a waveguide is a metal tube for channeling ultrahigh-frequency waves.

A "waveguide connector" as used herein, refers to a mechanical device for optically joining the locking together separable mating parts of a waveguide system. It is also known as a waveguide coupler.

The inventors have discovered that using a coupling medium instead of an air gap to couple between a monolithic substrate and a waveguide can reduce the coupling loss and decreases the reflections from the surface of the waveguide and the surface of the monolithic substrate. With the coupling medium, the coupling efficiency is greatly improved, the undesirable reflection to the spectrometer is reduced, and the alignment problem due to an air gap is revolved.

The inventors also discovered the use of a monolithic substrate in an optical assembly with higher refractive index over the interference layer, hence eliminating the need for coating an extra layer of a high refractive index material on the interference layer, between the interference layer and the monolithic substrate.

Figure 1:
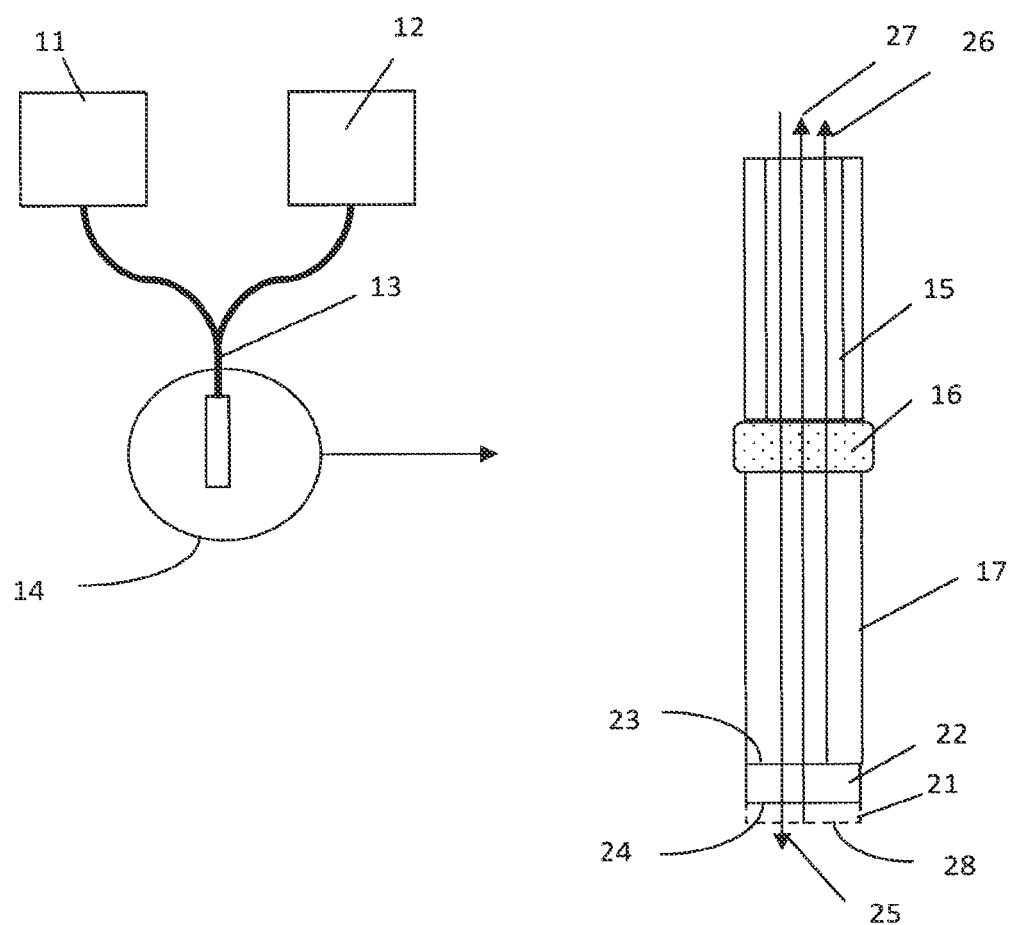
FIG. 1 illustrates the general embodiment of the present invention.

FIG. 1 illustrates a general embodiment of the present invention: a bio-sensor interferometer 10 comprising a light source 11, a detector 12, waveguide 13 and an optical assembly 14. The optical assembly 14 comprises the tip of the waveguide 15, a coupling medium 16, a monolithic substrate 17, a thin film layer (interference layer) 22 and a biomolecular layer 21. The thin film layer comprises a transparent material, a first reflecting surface comprising a layer of biomolecular molecules 21, and a second reflecting surface 23 between the thin film layer and the monolithic substrate. Also at the interface between the thin film layer 22 and the biomolecular layer 21 is a sensing surface 24.

A light source 11 in the apparatus can be a white light source, such as a light emitting diode (LED) which produces light over a broad spectrum, e.g., 400 nm or less to 700 nm or greater, typically over a spectral range of at least 100 nm. Alternatively, a light source can be a plurality of sources each having a different characteristic wavelength, such as LEDs designed for light emission at different selected wavelengths in the visible light range. The same function can be achieved by a single light source, e.g., white light source, with suitable filters for directing light with different selected wavelengths onto the optical assembly.

A detector 12 is preferably a spectrometer, such as Ocean Optics USB4000, capable of recording the spectrum of the reflected interfering light from the optical assembly. Alternatively, where the light source operates to direct different selected wavelengths onto the optical assembly, the detector can be a simple photodetector for recording light intensity at each of the different irradiating wavelengths. In still another embodiment, the detector can include a plurality of filters which allows detection of light intensity, e.g., from a white-light source, at each of a plurality of selected wavelengths of the interference reflectance wave.

A waveguide 13 transports a light signal from a light source to an optical assembly, and transports reflected light signals from the optical assembly to a detector. Commonly the waveguide comprises a fiber bundle. Spectrometer is a typical light detector used in bio-sensor interferometers.

A coupling medium 16 couples the waveguide and the monolithic substrate without leaving any gap between them. The coupling medium is an optically transparent material such as a polymer, an index matching gel, or an index matching liquid with a desired specific refractive index. An index matching liquid should have desired physical and chemical properties such as high viscosity, low vapor pressure (not easily evaporated) and a low corrosion rate. Suitable materials for the coupling medium comprise the following: polycarbonate, poly(methyl methacrylate) (PMMA), polystyrene (PS), polypropylene (PP), acrylonitrile butadiene styrene (ABS), refractive index matching gel, refractive index matching liquid, or polydimethylsiloxane (PDMS). Typically, the waveguide 13 comprises fiber material having a refractive index of approximately 1.5. Since the refractive index of the air gap is approximately 1.00, the presence of an air gap between the waveguide and the monolithic substrate would result in a coupling loss and high reflection. When the coupling medium couples the waveguide and the monolithic substrate without leaving any gap between them, the coupling efficiency is greatly improved, reflection is reduced, and alignment problems are alleviated. In a preferred embodiment, the refractive index of the coupling medium is in between the refractive indexes of the waveguide and the monolithic substrate.

A monolithic substrate made of a monolithic dielectric material is coupled to a tip of a waveguide through a coupling medium. The cross section of the monolithic substrate may be round, square, triangular, oval, or rectangular shaped. In a preferred embodiment, the aspect ratio of the monolithic substrate (length to width or length to diameter) is at least 5:1. The monolithic substrate material preferably has a refractive index that is substantially higher than that of the thin-film layer, such that the second reflective surface effectively reflects a portion of the light directed onto the optical assembly. The preferred refractive index of the monolithic substrate material is higher than 1.5, or higher than 1.8, or higher than 2.0. A preferred refractive index range of the monolithic substrate material is between about 1.55 to about 2.0. The monolithic substrate works effectively as an optical waveguide when the incident light enters the substrate proximal surface in a certain angle that still allows a total internal reflection. In this embodiment, this angle is defined by the combination of the numerical aperture of the lighting optic fiber, the substrate, and the mechanical coupling angel between the substrate and the lighting optic fiber.

An interference layer (a thin-film layer) is a transparent material coated on the sensing side of the monolithic substrate. Thin films are thin material layers ranging from fractions of a nanometer (monolayer) to several micrometers in thickness. Electronic semiconductor devices and optical coatings are the main applications benefiting from thin film construction. The thin-film layer of the present invention typically has a thickness of at least 50 nm, and preferably at least 100 nm. An exemplary thickness is between about 100-5,000 nm, preferably 400-1,000 nm. The refractive index of the thin-film layer material is preferably similar to that of the first reflecting surface, so that reflection from the lower distal end of the optical assembly occurs predominantly from the layer formed by the analyte-binding molecules, rather than from the interface between the optical element and the analyte-binding molecules. Similarly, as analyte molecules bind to the lower layer of the optical assembly, light reflection form the lower end of the assembly occurs predominantly from the layer formed by the analyte-binding molecules and bound analyte, rather than from the interface region. One exemplary material forming the thin-film layer is $SiO_2$, e.g., a high-quality glass having an index of refraction of about 1.4-1.5. The thin-film layer can also be formed of a transparent polymer as the monolithic substrate, such as polystyrene or polyethylene, having an index of refraction preferably in the 1.3-1.8 range.

The thickness of the biomolecular (analyte-binding molecular) layer 21 is designed to optimize the overall sensitivity based on specific hardware and optical components. Conventional immobilization chemistries are used in chemically, e.g., covalently, attaching a layer of analyte-binding molecules to the lower surface of the optical element. For example, a variety of bifunctional reagents containing a siloxane group for chemical attachment to $SiO_2$, and an hydroxyl, amine, carboxyl or other reaction group for attachment of biological molecules, such as proteins (e.g., antigens, antibodies), or nucleic acids. It is also well known to etch or otherwise treat glass a glass surface to increase the density of hydroxyl groups by which analyte-binding molecules can be bound. When the thin-film layer is formed of a polymer, such as polystyrene, a variety of methods are available for exposing available chemically-active surface groups, such as amine, hydroxyl, and carboxyl groups.

The analyte-binding layer is preferably formed under conditions in which the distal surface of the optical element is densely coated, so that binding of analyte molecules to the layer forces a change in the thickness of the layer, rather than filling in the layer. The analyte-binding layer can be either a monolayer or a multi-layer matrix.

The measurement of the presence, concentration, and/or binding rate of analyte to the optical assembly is performed by the interference of reflected light beams from the two reflecting surfaces in the optical assembly. Specifically, as analyte molecules attach to or detach from the surface, the average thickness of the first reflecting layer changes accordingly. Because the thickness of all other layers remains the same, the interference wave formed by the light waves reflected from the two surfaces is phase shifted in accordance with the thickness change due to the analyte binding.

The use of a monolithic substrate material instead of an optic fiber in the optical assembly has several advantages. In a preferred embodiment, the refractive index of the monolithic substrate is higher than the refractive index of the transparent material of the thin-film layer. Because the monolithic substrate is a single solid material, therefore, it is easy to select a material having higher refractive index than that of the thin-film layer. On the contrary, an optic fiber is typically a circular cross-section dielectric waveguide consisting of a dielectric material (a core material) surrounded by another dielectric material with a lower refractive index (cladding); therefore, it is difficult to manipulate its refractive index. In the prior art (U.S. Pat. No. 7,394,547), the refractive indexes of the optical sensor fiber and the interference layer are essentially the same having values of approximately 1.46. Hence, the prior art requires an extra coating of a high refractive material on top of the interference layer in order to properly reflect the incident light.

In operation, incident light signal 25 is emitted from the light source 11 and is transported through the waveguide 13 wherein the incident light signal 25 is coupled through the coupling medium 16 to the monolithic substrate 17 and subsequently coupled to the thin film layer and the biomolecular layer 21. Within the optical assembly 14, light is reflected at the second reflecting surface 23 resulting in a reflected light signal 26. Additionally, light is reflected at the first reflecting surface 28 resulting in the reflected light signal 27. Before analyte binding, the first reflecting surface is a surface between a layer of biomolecules (analyte binding molecules) 21 and the sample solution. After analyte binding, the first reflecting surface becomes the surface between a layer analyte molecules and the sample solution.

Figure 2:
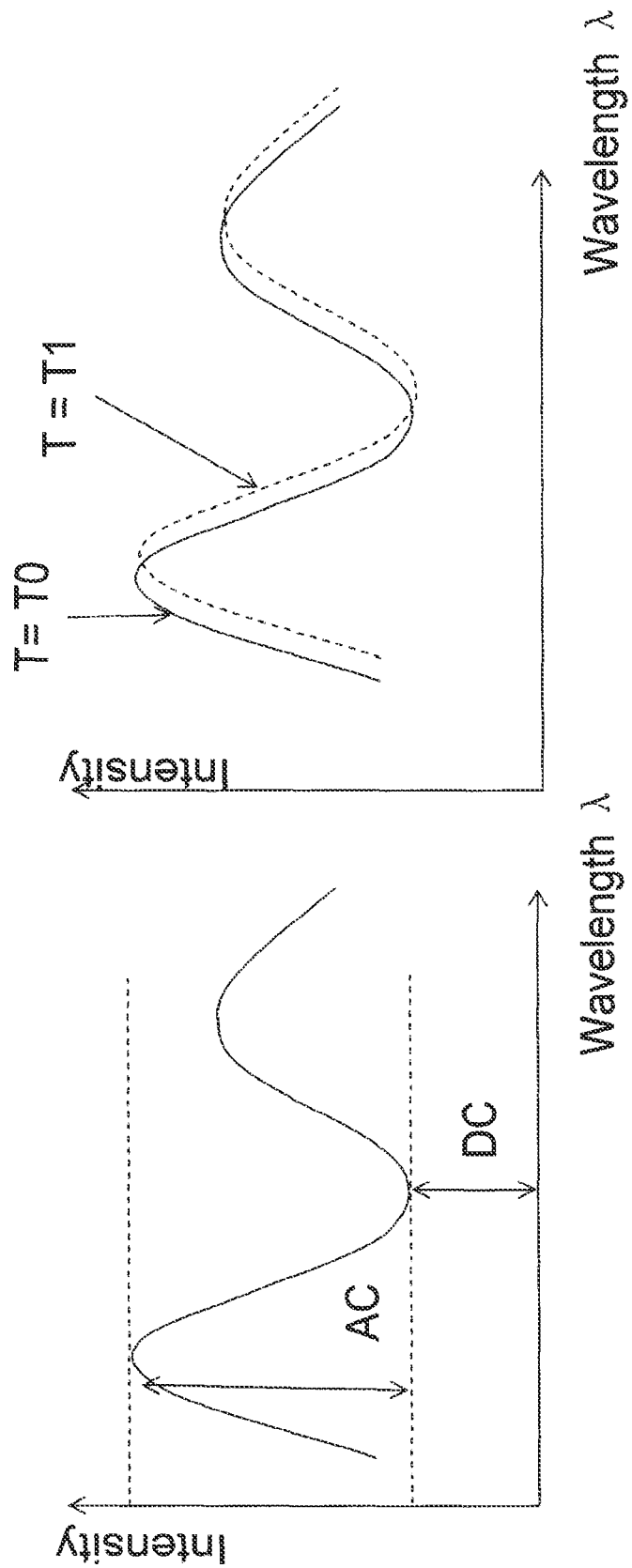
FIGS. 2A and 2B illustrate the principles of detection in a thin-film interferometer.

The two light signals reflected from boundaries between first and second refracting surfaces generate a spectral interference pattern, as shown in FIG. 2a. When biomolecules bind to analyte molecules on the peripheral surface of the thin-film layer (interference layer), the second reflection signal's equivalent optical path extends. As a result, the spectral interference pattern shifts from T0 to T1 as shown in FIG. 2b. By measuring the pattern's phase shift continuously in real-time, a kinetic binding curve can be measured as the amount of shift vs. the time. The association rate of an analyte to a capture molecule immobilized on the surface can be used to calculate the analyte's concentration. Hence, the measurement of this phase shift is the detection principle of a thin-film interferometer.

Referring to FIG. 2a, the performance of the bio-sensor interferometer is improved as the AC component is maximized and the DC offset is minimized. To achieve these objectives, one must increase the coupling efficiency for the incident light signal 25 from the light source 11 to the sensing surface 24 and the coupling efficiency for the reflected light signals 26 and 27 from the first and second refracting surfaces to the spectrometer 12. Concurrently, the reflection from the other interfaces should be reduced as much as possible.

Figure 3:
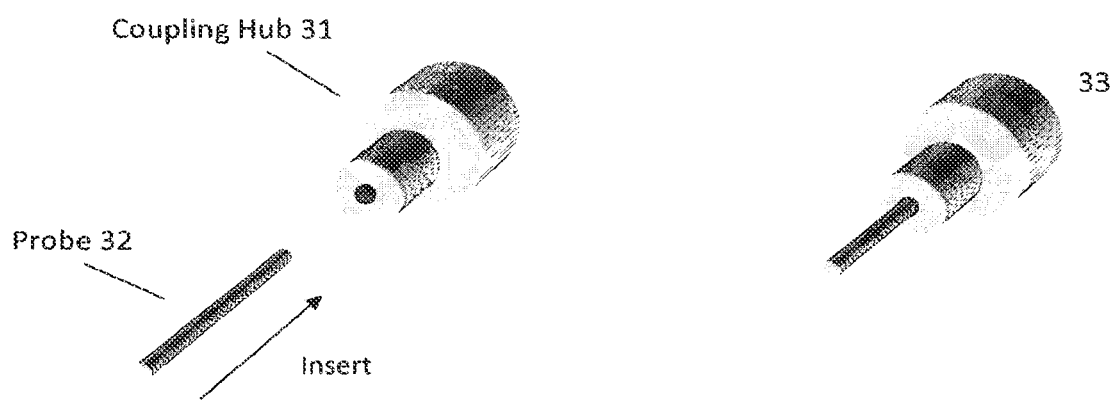
FIG. 3 illustrates a probe inserted into a coupling hub.
Figure 4:
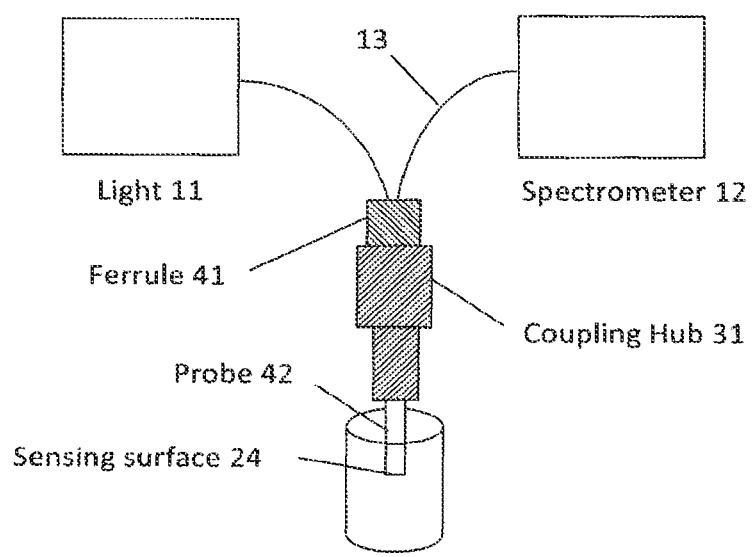
FIG. 4 illustrates a biosensor with a coupling hub.

In one embodiment, the present invention comprising a coupling hub is illustrated in FIG. 3, where a probe 32 is inserted into the center bores of the molded plastic 31 and results a structure 33. The probes were then inserted into the center bores of the molded plastic hub. FIG. 4 shows a simplified illustration of the bio-sensor based on thin film interferometer. The bio-sensor comprises light source 11, spectrometer 12, waveguide 13, ferrule 41, coupling hub 31, probe 42, and sensing surface 24. The tip of the probe and the sensing surface 24 are dipped into a coating solution containing analyte-binding molecules.

This invention is directed to an assembly for use in detecting an analyte in a sample based on thin-film spectral interference. The assembly comprises: (a) a waveguide connector containing a waveguide, wherein the waveguide transports a light signal from a light source to the assembly, and the waveguide transports reflected light signals from the assembly to a detector; (b) a monolithic substrate having a coupling side and a sensing side, the coupling side is coupled to the waveguide connector with the waveguide by a coupling hub; (c) a coupling medium located between the waveguide connector and the monolithic substrate so the waveguide optically couples with the monolithic substrate without any gap; and (d) a thin-film layer directly bonded to the sensing side of the monolithic substrate, wherein the thin film layer comprises a transparent material, a first reflecting surface comprising a layer of analyte binding molecules, and a second reflecting surface between the thin film layer and the monolithic substrate; whereby a spectral interference between light reflected into the waveguide from the assembly varies as analyte molecules in the sample bind to the analyte binding molecules.

In one embodiment, the coupling hub is inserted into the waveguide connector. In another embodiment, the waveguide connector is a ferrule and the ferrule is inserted into the coupling hub.

In one embodiment, the coupling hub comprises the coupling medium. In another embodiment, the waveguide connector is a ferrule and the coupling medium is between the ferrule and the bottom of the coupling hub.

Figure 5:
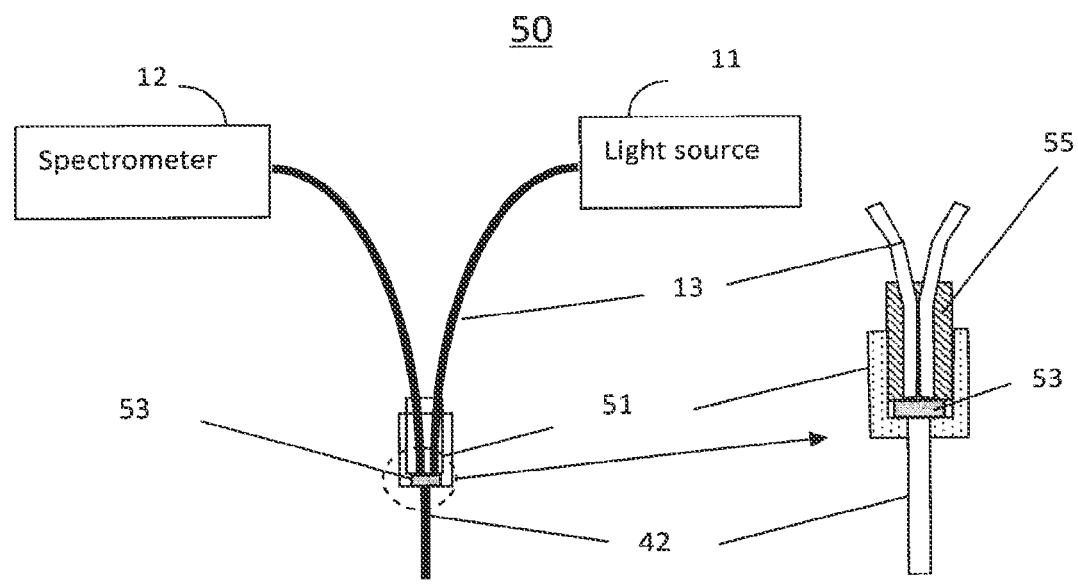
FIG. 5 illustrates the present invention implemented with a coupling hub.

In FIG. 5, bio-sensor 50 illustrates the present invention implemented with a coupling hub 51. Bio-sensor 50 is an assembly for use in detecting an analyte in a sample based on thin-film spectral interference. Bio-sensor 50 comprises a ferrule 55 containing a waveguide 13, wherein the waveguide 13 transports the incident light signals from the light source 11 to the coupling hub 51 and transports reflected light signals from the coupling hub 51 to the spectrometer 12 (detector). Bio-sensor 50 further comprises a probe 42, which is coupled to the ferrule 55 with the waveguide 31 by a coupling hub 51, and ferrule 55 is inserted into the coupling hub 51. Within the coupling hub 51, a coupling medium 53 is located between the ferrule 55 and the probe 52 so the end of the waveguide 31 directly contacts the monolithic substrate of the probe 42 without any gap, such as an air gap.

Figures 6A, 6B, 6C:
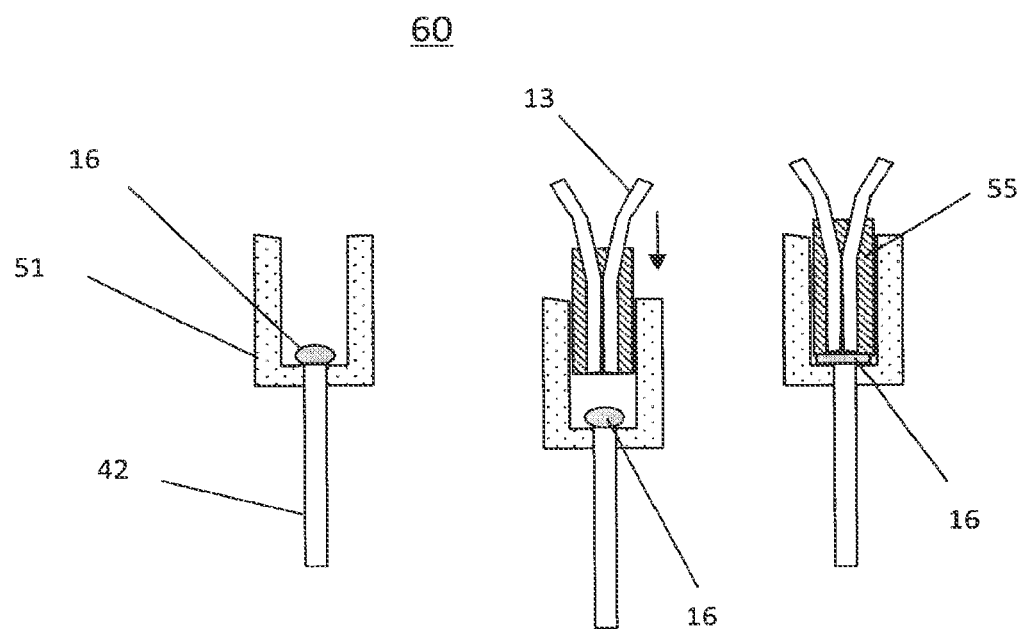
FIG. 6A-C illustrates one coupling hub embodiment with coupling medium pre-installed inside the hub.

FIG. 6 illustrates one coupling hub embodiment of FIG. 5 with a coupling hub assembly 60. Coupling hub 51 has a coupling medium 16 pre-installed inside and at the bottom of coupling hub 51, as indicated in FIG. 6a. Probe 42 contacts the coupling medium 16 at the bottom of the hub. As illustrated in FIG. 6b, a ferrule 55 with a fiber bundle (waveguide 13) is inserted into coupling hub 51. As illustrated in FIG. 6c, the coupling medium 16 connects probe 42 and the instrument fiber bundle (waveguide 13) without a gap. Hence, the coupling medium 16 is located between the ferrule 55 and the bottom of the coupling hub 51.

Figures 7A, 7B, 7C, 7D, 7E:
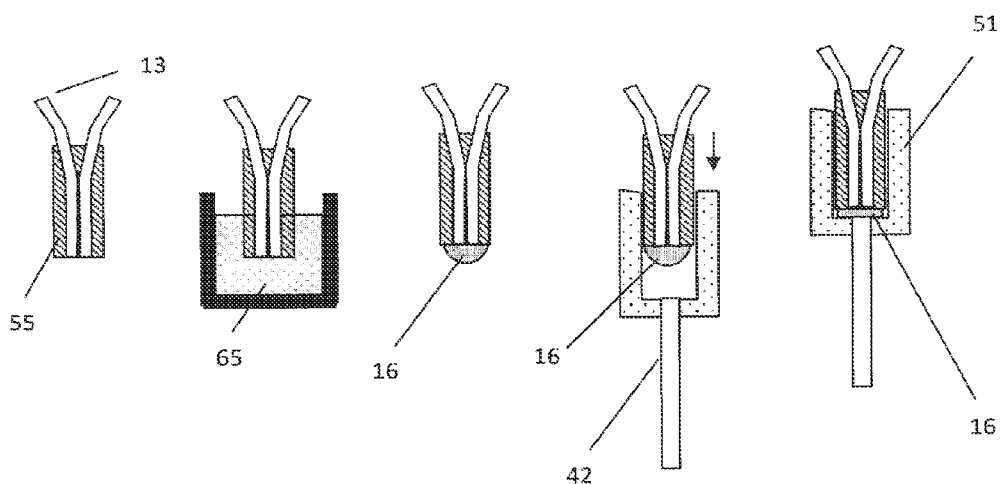
FIG. 7A-E illustrates a second coupling hub embodiment with a drop of coupling medium formed on the tip of the ferrule.

FIG. 7 illustrates a second coupling hub embodiment of FIG. 5 with coupling hub assembly 70 having a droplet of coupling medium formed on the tip of the ferrule. FIG. 7a shows a ferrule 55 with fiber bundle (waveguide 13), which is dipped into a reservoir 65 of coupling medium of index matching gel or liquid (FIG. 7b). In FIG. 7c, the ferrule 55 with fiber bundle (waveguide 13) is removed from the reservoir 65 resulting in a droplet of coupling medium 16 formed on the tip of the ferrule 55. In FIG. 7d, the resulting ferrule 55 with fiber bundle (waveguide 13) is inserted into coupling hub 51. The result is that the drop of the coupling medium 16 connects probe 42 and the instrument fiber bundle (waveguide 13) with zero gap coupling, as illustrated in FIG. 7e. Hence, the drop of coupling medium 16 is located between the ferrule 55 and the bottom of the coupling hub 51.

Figures 8A, 8B, 8C:
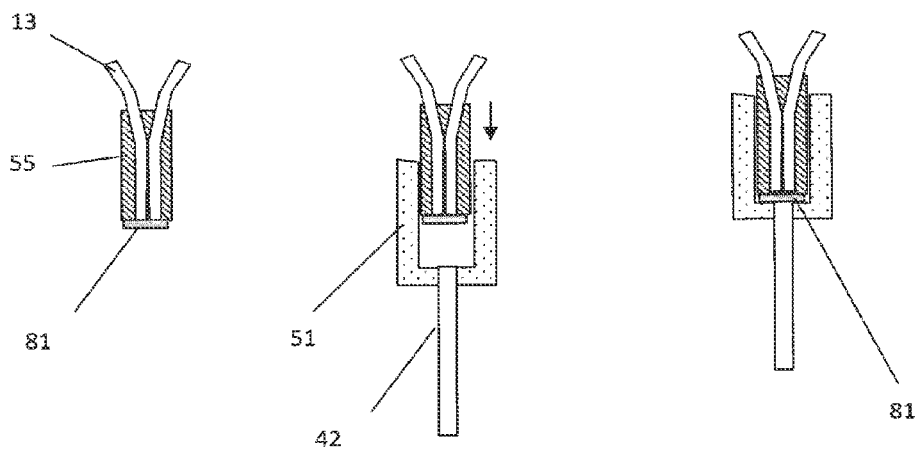
FIG. 8A-C illustrates a third coupling hub embodiment with a coupling medium attached to the ferrule.

FIG. 8 illustrates a third coupling hub embodiment of FIG. 5 with coupling hub assembly 80 having a coupling medium 81 pre-installed on ferrule 55, as indicated in FIG. 8a. In FIG. 8b, the ferrule 55 with coupling medium 81 and with fiber bundle (waveguide 13) is inserted into coupling hub 51. The result is that coupling medium 81 connects probe 42 and the instrument fiber bundle (waveguide 13) without any gap, as illustrated in FIG. 8c. Hence, the coupling medium 81 is located between the ferrule 55 and the bottom of the coupling hub 51.

Figure 9A:
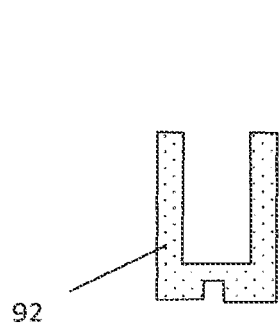
FIG. 9A-B illustrates a fourth coupling hub embodiment with the coupling hub comprising a coupling medium.
Figure 9B:
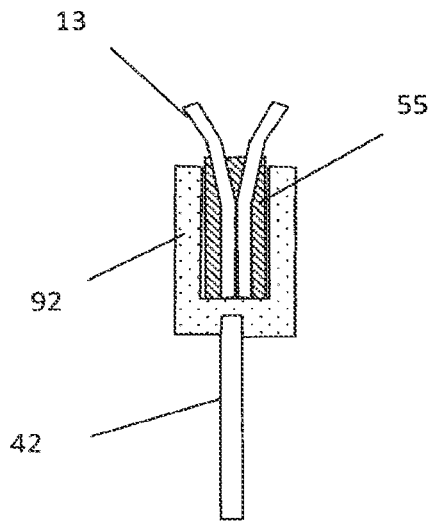

FIG. 9 illustrates a fourth coupling hub embodiment of FIG. 5 with coupling hub assembly 90 comprising a coupling medium such as a polymer material. As shown in FIG. 9a, coupling hub 92 comprises a coupling medium. In FIG. 9b, a ferrule 55 with fiber bundle (waveguide 13) is inserted into coupling hub 51. The result is that ferrule 55 contacts the bottom of coupling hub 92 and the probe 42 contacts the opposite side of the coupling hub 92 resulting in zero gaps coupling between the ferrule 55 and probe 42.

Figures 10A, 10B, 10C:
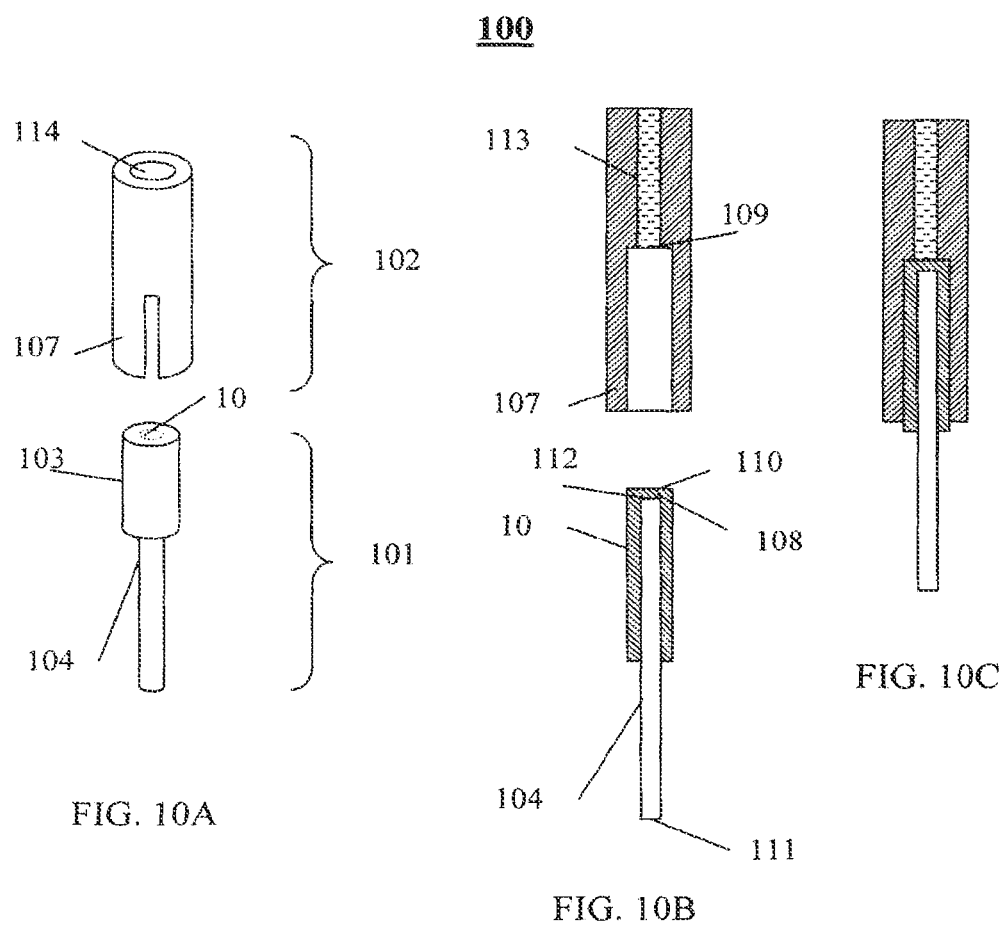
FIG. 10A-C illustrates another coupling hub embodiment with the coupling hub comprising a coupling medium.

FIG. 10a-10c show another coupling hub embodiment with coupling hub assembly 100. Assembly 100 comprises waveguide connector 102 and the removable probe 101. FIG. 10a is a perspective view showing the waveguide connector 102 and the removable probe 101 unattached to each other. The wave guide connector 102 has a hole 114 in the top where the waveguide (e.g. fiber) is inserted. FIG. 10b is a cross-section view of the waveguide connector 102 and the removable probe 101 unattached to each other. FIG. 10c shows the removable probe 101 inserted into the waveguide connector 102.

Referring first to FIG. 10a, the removable probe 101 consists of a monolithic substrate 104, which is coatd with a thin-film layer, and a cylindrical shaped coupling hub 103, which has a hole 105 in the center. The monolithic substrate 104 is deposited with a thin-film coating such as a $SiO_2$ layer and analyte binding molecules. The monolithic substrate 104 is in a rod shape with its length at least 5 times greater than the diameter. As shown in FIG. 10b, the removal probe has a sensing surface 111 for detecting analyte and a coupling surface 112. In one design, the hub 103 is made from transparent plastics. The hole 105 in the hub 103 is not a through hole with one end having a layer 108 of the same transparent plastic material as the hub 103. Layer 108 is the top of cylindrical shaped hub 103. The substrate 104 is fixedly attached to the hub 103 by inserting the substrate's coupling surface against the inside wall of coupling surface 112 of the layer 108.

This layer 108 serves as an optical coupling medium between the substrate's coupling surface 112 and the waveguide 113 that is installed inside the waveguide connector 102. The waveguide connector shown here has flexible gripping arms 107 to engage the hub 103 and maintain enough fictional force to hold the substrate 104 in place relative to the waveguide 113.

The inside of the waveguide connector 102 has a flat engagement surface 109 that is flushed with the waveguide's surface. The hub 103 has a flat top surface 110. When engaged, the top surface 110 is pushed against the engagement surface 109 so that the gap between the two surfaces are completely closed. The layer 108 as a coupling medium is sandwiched between the coupling surface 112 of the substrate 104 and the waveguide 113. With a coupling medium having the refractive index greater than the air, preferably between the waveguide 113 and the substrate 104, will enhance the coupling efficiency, minimize the undesirable reflections back to the spectrometer, and reduce the sensitivity of the lateral misalignment between the substrate 104 and the waveguide 113.

FIG. 10c illustrates the engagement of the waveguide connector 102 and the removable probe 101.

Figures 11A, 11B, 11C:
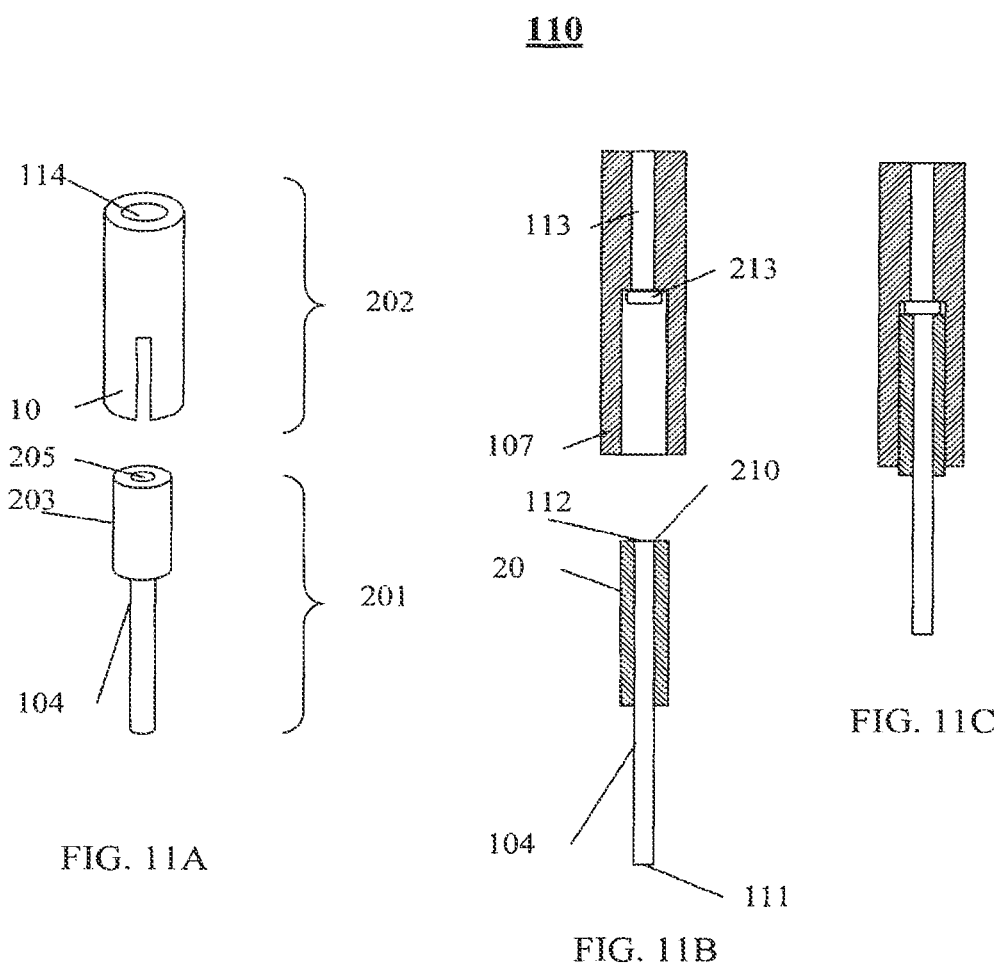
FIG. 11A-C illustrates another coupling hub embodiment with the coupling medium attached to the waveguide connector.

FIG. 11a-11c show details of another coupling hub embodiment with coupling hub assembly 110. Assembly 100 comprises of waveguide connector 202 and the removable probe 201. FIG. 11a is a perspective view showing the waveguide connector 202 and the removable probe 201 unattached to each other. FIG. 11b is a cross-section view of the waveguide connector 202 and the removable probe 201 unattached to each other. The wave guide connector 202 has a hole 114 in the top where the waveguide (e.g. fiber) is inserted. FIG. 11c shows the removable probe 201 inserted into the waveguide connector 202.

Referring first to FIG. 11a, the removable probe 201 consists of a monolithic substrate 104 in a rod shape with its length at least 5 times greater than the diameter, and a cylindrical shaped hub 203 that has a hole 205 in the center. As shown in FIG. 11b, the substrate 104 has a sensing surface 111 and a coupling surface 112. The hub 203 is made from transparent plastics. The substrate 104 is fixedly attached to the hub 203 by inserting the substrate into the hole until the coupling surface 112 flush with the hub's top surface 210. The sensing surface 111 is deposited with a thin-film coating that includes a SiO2 layer and analyte binding molecule that can be used for detecting analyte.

A coupling medium 213 is installed inside the waveguide connector 202 at the end of the waveguide 113. The coupling medium is preferred to choose from optically transparent, elastic materials or liquid-like materials. PDMS is an example. The waveguide connector 202 shown here has flexible gripping arms 107 to engage the hub 203 and maintain enough fictional force to hold the substrate 104 in place relative to the waveguide 113.

When engaged, the hub's top surface 210 is pushed against the coupling medium 213 so that the gap between the waveguide 113 and the substrate 104 is completely closed. The coupling medium 213 is sandwiched between the coupling surface 112 of the substrate 104 and the waveguide 113. With a coupling medium having the refractive index greater than the air, preferably between the waveguide 113 and the substrate 104, will enhance the coupling efficiency, minimize the undesirable reflections back to the spectrometer, and reduce the sensitivity of the lateral misalignment between the substrate 104 and the waveguide 113.

FIG. 11c illustrates the engagement of the waveguide connector 202 and the removable probe 201.

Figure 12:
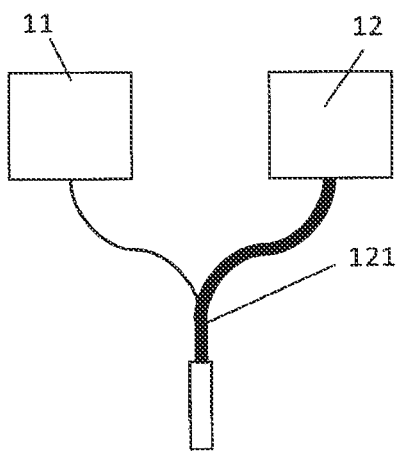
FIG. 12 illustrates a Y coupler with uneven branches.

As previously noted, a waveguide may be provided by a Y-shaped optic fiber coupler (Y-coupler). An improved embodiment of a Y-shaped optic fiber coupler is illustrated in FIG. 12. Embodiment 100 comprises a light source 11, a spectrometer 12, and a Y-coupler with uneven branches 121 coupled to the light source 11 and spectrometer 12. In order to improve the performance of the bio-sensor, the size of the connection to the spectrometer 12 (detector) is designed to be larger that the size of the connection to the light source 11. As shown in FIG. 12, when a Y-shape optic fiber coupler is used, it is preferred to fuse an optic fiber having a smaller diameter with an optic fiber having a larger diameter. The smaller arm will be used for the illuminating light from light source 11 and the larger one for the spectrometer 12. This configuration will enable more reflecting light go to the spectrometer 12, thus improve the overall coupling efficiency.

The present invention is also directed to an assembly for use in detecting an analyte in a sample based on thin-film spectral interference. The assembly comprises: (a) a waveguide; (b) a monolithic substrate having a coupling side and a sensing side, the coupling side is optically coupled to the waveguide; (c) a thin-film layer directly bonded to the sensing side of the monolithic substrate; wherein the waveguide transports a light signal from a light source to the assembly, and the waveguide transports reflected light signals from the assembly to a detector; the thin film layer comprises a transparent material, a first reflecting surface comprising a layer of analyte binding molecules, and a second reflecting surface between the thin film layer and the monolithic substrate; the refractive index of the monolithic substrate is higher than the refractive index of the transparent material of the thin-film layer; whereby a spectral interference between light reflected into the waveguide from said first and said second reflecting surfaces varies as analyte molecules in the sample bind to the analyte binding molecules. In this assembly, all the terms have the same characteristics as those recited before.

In one design, the assembly eliminates the gap between the waveguide and the monolithic substrate by connecting them end to end. Alternatively, the assembly further comprises a coupling medium between the waveguide and the monolithic substrate to fill any gap in between. The refractive index of the coupling medium is in general greater than about 1.3, preferably in between refractive indexes of the waveguide and the monolithic substrate.

In yet another design, there is a gap between the waveguide and the monolithic substrate.

The apparatuses described in this application can be used for the following applications: (i) with an anti-species antibody carried on the tip, for screening hybridoma expression lines for cell lines with high antibody expression; (ii) with an antigen carried on the tip, to characterize high affinity antibodies against that antigen; (iii) with a protein carried on the tip, for identifying and characterizing binding partners (DNA, RNA, proteins, carbohydrates, organic molecules) for that protein; (iv) with a carbohydrate or glycosyl moiety carried on the tip, for identifying and characterizing binding partners (such as, e.g., DNA, RNA, proteins, carbohydrates, organic molecules) for that carbohydrate; (v) with a protein that participates in a multi-protein complex carried on the tip, for characterizing the binding components and/or kinetics of complex formation; (vi) with a small protein-binding molecule carried on the tip, for identifying and characterizing protein binders for that molecule; (vii) with an antibody carried on the tip, for constructing a calibration curve for the analyte using a set of analytes standards. Using this calibration curve, one can then determine the concentration of the analyte in unknown solutions (cell culture supernatants, biological samples, process mixtures, etc). (viii) with a single-stranded nucleic acid, e.g., ssDNA or RNA carried on the tip, for identifying and molecules that bind specifically to the nucleic acid.

The invention is illustrated further by the following examples that are not to be construed as limiting the invention in scope to the specific procedures described in them.

EXAMPLES

Example 1

Preparation of Streptavidin Probes

A glass rod (a monolithic substrate), 1 mm diameter and 2 cm in length, had both coupling end and sensing end polished. The sensing end was first coated with a $SiO_2$ coating layer (a thin-film layer) with a thickness of 650 nm using a physical vapor deposition technology, and then deposited with aminopropylsilane (APS) using a chemical vapor deposition process (Yield Engineering Systems, 1224P) following manufacturer's protocol. APS is deposited to enable protein immobilization. APS adsorbs protein to the surface of the probe by a combination of hydrophobic and ionic interaction. Protein can also be coupled to the amino group of APS by covalent coupling using a crosslinking reagent. APS is only a monolayer, about 7 nm thick.

The probe (the glass rod coated with $SiO_2$ and APS) was then inserted into the center bores of the molded plastic hubs, as shown in FIG. 3. The probe was then locked to the hub by either adhesive or a locking mechanism.

The probe tip with the sensing end was then immersed in a solution of streptavidin (Scripps Labs), 50 µg/ml in phosphate buffered saline pH 7.4 (PBS). After allowing the streptavidin to adsorb to the probe for 5 minutes, the probe tip was washed in PBS, then immersed in a solution of 10% sucrose for 30 seconds followed by drying at 30° C. for one hour and then stored in a dry condition. Typically, the probe is at least 0.5 mm immersed.

Example 2

Detection of Protein A Binding to Human IgG

Figure 13:
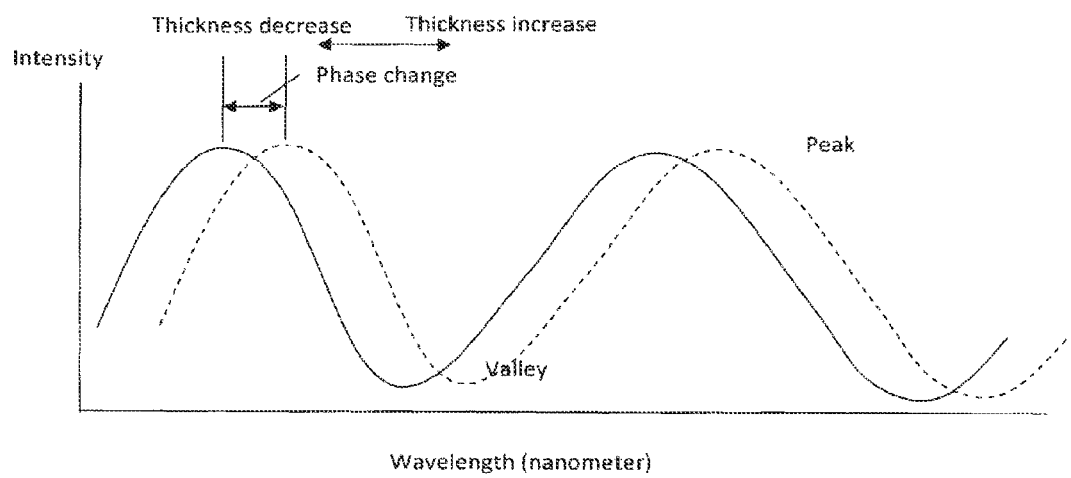
FIG. 13 illustrates a typical interference pattern of a binding assay detected by a thin-film interferometer.

As shown in FIG. 3, each probe was first connected to waveguides in a ferrule. The waveguides connect to a halogen light source and a spectrometer so the light will be transported to the probe's sensing surface and reflected light will be transported to the spectrometer for measurement. Multiple of such systems can be set up to achieve parallel detection. The spectrometers measure the reflected light from the sensing ends of the probes and output spectral interference patterns in a real-time function of wavelengths and light intensity at each wavelength. A typical interference pattern is shown in FIG. 13. A phase change in the form of left shift of the peaks and valleys represents a reduction of the thin-film thickness (disassociation of molecules on the sensing surface); and a right shift means an increase of the thin-film thickness (association of molecules on the sensing surface). By converting the interference pattern to a digital format, a computer is used to determine the amount of thickness change at any time instance. A binding curve (or association and disassociation curve) can be graphed with respect to the time. Kinetics of molecular interactions between two different molecules, one in solution and one immobilized on a probe's sensing surface, can thus be analyzed. In a quantization assay, the concentration of the analyte molecules in solution can be derived from the kinetics: faster binding kinetics implies higher concentration of analyte.

Figure 14:
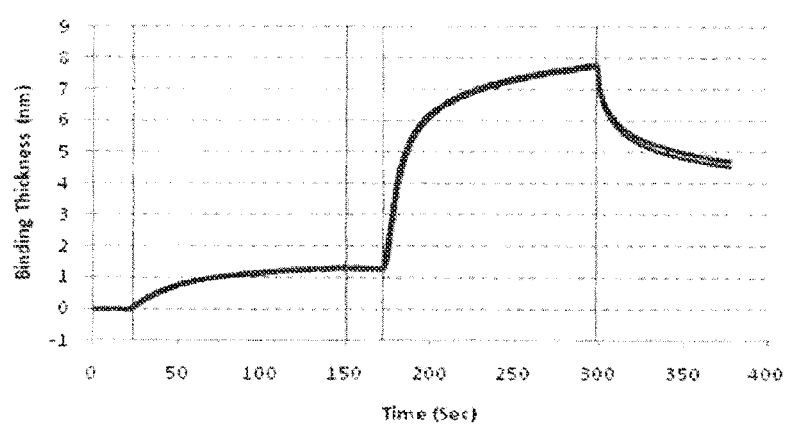
FIG. 14 illustrates the association and dissociation curves of two probes simultaneously.

An example is demonstrated with two probes measured in parallel. FIG. 14 shows the association and disassociation curves of two probes simultaneously.

To start the analysis, the probe's sensing ends were immersed in PBS for about 20 seconds to hydrate the immobilized streptavidin (Step 1). This step was also used to establish a baseline for the binding curve. The probes were then transferred to a biotinylated Protein A sample (Pierce Chemical) at 50 µg/ml concentration in PBS in Step 2. After about 100 seconds there was about a 1 nm shift. Step 3 entailed a brief wash of the probe sensing ends in PBS. Step 4 shows the binding to Human IgG (Jackson ImmunoResearch) at 0.1 mg/ml concentration in PBS to the Protein A coated probe sensing ends. In about two minutes, the total thickness of the thin-film layer ($SiO_2$ coating) plus biomolecular layer increased by 6.5 nm (Step 4). To disassociate the IgG/Protein A complex, the probes were transferred to sodium acetate solution at pH 4. In about 75 seconds the thin-film thickness decreased by 3 nm (Step 5).

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. An assembly for use in detecting an analyte in a sample based on thin-film spectral interference, comprising:
   a waveguide connector containing a waveguide;
   a monolithic substrate having a coupling side and a sensing side, wherein the coupling side is coupled to the waveguide connector;
   a coupling medium located between the waveguide connector and the monolithic substrate, wherein the refractive index of the monolithic substrate is higher than the refractive index of the waveguide, and the refractive index of the coupling medium is in between the refractive indexes of the monolithic substrate and the waveguide; and
   a thin-film layer directly bonded to the sensing side of the monolithic substrate,
   wherein the thin film layer comprises a transparent material, a first reflecting surface comprising a layer of analyte binding molecules, and a second reflecting surface between the thin film layer and the monolithic substrate,
   wherein the waveguide is configured to transport a light signal from a light source to the sensing side of the monolithic substrate, and the waveguide is further configured to transport light signals from the sensing side of the monolithic substrate to a detector;
   whereby a spectral interference between light reflected into the waveguide from said first and said second reflecting surfaces varies as analyte molecules in the sample bind to the analyte binding molecules.

2. The assembly as in claim 1, wherein the refractive index of the monolithic substrate is higher than the refractive index of the transparent material of the thin-film layer.

3. The assembly as in claim 1, wherein the refractive index of the coupling medium is greater than 1.3.

4. The assembly as in claim 1, wherein the monolithic substrate is a sensor fiber.

5. The assembly according to claim 1, wherein the length to width or length to diameter aspect ratio of the monolithic substrate is at least 5 to 1.

6. The assembly according to claim 1, wherein the monolithic substrate is made of glass, quartz, or plastic.

7. The assembly according to claim 1, wherein the refractive index of the monolithic substrate is at least 1.55.

8. The assembly according to claim 1, further comprising a Y-shaped fiber optic coupler having a first branch, a second branch and a third branch, wherein the first branch is configured to couple to the light source, the second branch is configured to couple to the detector, the third branch couples to the waveguide, and the second branch has a larger diameter than the first branch.

9. The assembly according to claim 1, wherein the coupling medium has a diameter larger than a diameter of the monolithic substrate.

10. An assembly for use in detecting an analyte in a sample based on thin-film spectral interference, comprising:
a waveguide;
a monolithic substrate having a coupling side and a sensing side, wherein the coupling side is optically coupled to the waveguide;
a thin-film layer directly bonded to the sensing side of the monolithic substrate;
a coupling medium located between the waveguide and the monolithic substrate and
the thin film layer comprises a transparent material, a first reflecting surface comprising a layer of analyte binding molecules, and a second reflecting surface between the thin film layer and the monolithic substrate;
wherein the refractive index of the monolithic substrate is higher than the refractive index of the waveguide, and the refractive index of the coupling medium is in between the refractive indexes of the monolithic substrate and the waveguide;
wherein the coupling medium has a diameter larger than a diameter of the monolithic substrate;
wherein the waveguide is configured to transport a light signal from a light source to the sensing side of the monolithic substrate, and the waveguide is further configured to transport light signals from the sensing side of the monolithic substrate to a detector;
wherein the refractive index of the monolithic substrate is higher than the refractive index of the transparent material of the thin-film layer; and
whereby a spectral interference between light reflected into the waveguide from said first and said second reflecting surfaces varies as analyte molecules in the sample bind to the analyte binding molecules.

11. The assembly according to claim 10, wherein the refractive index of the coupling medium is greater than 1.3.

12. The assembly according to claim 10, wherein the length to width or length to diameter aspect ratio of the monolithic substrate is at least 5 to 1.

13. The assembly according to claim 10, wherein the monolithic substrate is made of glass, quartz, or plastic.

14. The assembly according to claim 10, wherein the refractive index of the monolithic substrate is at least 1.55.

15. The assembly according to claim 10, further comprising a Y-shaped fiber optic coupler having a first branch, a second branch and a third branch, wherein the first branch is configured to couple to the light source, the second branch is configured to couple to the detector, the third branch couples to the waveguide, and the second branch has a larger diameter than the first branch.

* * * * *